(12) United States Patent
Powell et al.

(10) Patent No.: US 11,000,502 B2
(45) Date of Patent: May 11, 2021

(54) ANTIMICROBIAL COMPOSITIONS COMPRISING COPPER-HYDROXYPYRONE COMPLEXES

(71) Applicant: United Kingdom Research and Innovation, Swindon (GB)

(72) Inventors: Jonathan Joseph Powell, Cambridge (GB); Nuno Jorge Rodrigues Faria, Milton Ernest (GB); Carlos Andre Passos Bastos, Cambridge (GB)

(73) Assignee: United Kingdom Research and Innovation, Swindon (GB)

( * ) Notice: Subject to any disclaimer, the term of this patent is extended or adjusted under 35 U.S.C. 154(b) by 0 days.

(21) Appl. No.: 16/480,363

(22) PCT Filed: Feb. 6, 2018

(86) PCT No.: PCT/EP2018/052958
§ 371 (c)(1),
(2) Date: Jul. 24, 2019

(87) PCT Pub. No.: WO2018/141989
PCT Pub. Date: Aug. 9, 2018

(65) Prior Publication Data
US 2019/0380996 A1    Dec. 19, 2019

(30) Foreign Application Priority Data

Feb. 6, 2017 (GB) .................................. 1701944

(51) Int. Cl.
| | |
|---|---|
| *A61K 31/351* | (2006.01) |
| *A61K 33/34* | (2006.01) |
| *A61K 47/34* | (2017.01) |
| *A61P 31/04* | (2006.01) |
| *A61P 17/02* | (2006.01) |
| *A61P 31/10* | (2006.01) |
| *A61K 9/06* | (2006.01) |

(52) U.S. Cl.
CPC .............. *A61K 31/351* (2013.01); *A61K 9/06* (2013.01); *A61K 33/34* (2013.01); *A61K 47/34* (2013.01); *A61P 17/02* (2018.01); *A61P 31/04* (2018.01); *A61P 31/10* (2018.01)

(58) Field of Classification Search
None
See application file for complete search history.

(56) References Cited

U.S. PATENT DOCUMENTS 6,287,541 B1    9/2001  Creeth et al.
6,552,072 B2 *  4/2003  Thompson ............. A61K 33/30
                                            514/456

FOREIGN PATENT DOCUMENTS

| JP | 2002-255956 A | 9/2002 |
|---|---|---|
| WO | 00/16736 A1 | 3/2000 |
| WO | 0116736 A1 | 3/2000 |

OTHER PUBLICATIONS

Edited by Rowe et al., (2009), "Handbook of Pharmaceutical Excipients (6th ed.)", London: APhA, (PhP) Pharmaceutical Press., pp. 393-396 and 517-522. (Year: 2009).*
Kiran, Ravi K., "Synthesis Characterization and Antibacterial Activity of Cu(II), Zn(II) Ternary Complexes with Maltol and Glycylglycine," Chem. Sci. Trans., 3(2):592-601, 2014.
Thompson et al., "Metal complexes of maltol and close analogues in medicinal inorganic chemistry," Chem. Soc. Rev., 35(6):545-556, 2006.
Vishwakarma, Pradeep Kumar, "Pyrone-based Cu(II) complexes, their characterization, DFT based conformational drift from square planar to square pyramidal geometry and biological activities," J. Chem. Sci. 128(4):511-522, 2016.
International Search Report and Written Opinion issued in PCT/EP2018/052958, dated Apr. 20, 2018, 14 pages.
Hudecova et al., "New Azidometalkojates and their Biological Activity," Folia Microbiol. 41(6):473-476, 1996.
Search Report issued in GB Application No. 01701944.9, dated Jan. 11, 2018, 5 pages.

* cited by examiner

*Primary Examiner* — My-Chau T. Tran
(74) *Attorney, Agent, or Firm* — McNeill Baur PLLC

(57) ABSTRACT

Copper based antibacterial agents are described based on amphiphilic copper complexes formed between copper and hydroxypyrones, such as maltol. In further aspects, the present invention relates to PEG based-ointments showing that they are particularly effective for topical delivery of amphiphilic complexes of copper. In particular, PEG ointments were shown to limit bacterial growth, even when in the absence of copper agent. However, this bacteriostatic effect is shown herein to become a true biocidal effect when copper hydroxypyrones are added to the PEG.

17 Claims, 5 Drawing Sheets

ANTIMICROBIAL COMPOSITIONS COMPRISING COPPER-HYDROXYPYRONE COMPLEXES

CROSS-REFERENCE TO RELATED APPLICATIONS

This application is a national phase entry pursuant to 35 U.S.C. § 371 of International Application No. PCT/EP2018/052958, filed Feb. 6, 2018, which claims the benefit of priority of GB Application No. 1701944.9, filed Feb. 6, 2017, each of which is incorporated by reference herein in its entirety for any purpose.

FIELD OF THE INVENTION

The present invention relates to compositions comprising polyalkylene glycol and a copper hydroxypyrone complex and their uses as antimicrobial agents. The present invention further relates to medical uses of the compositions, in particular for wound healing and/or the treatment or prevention of microbial infection.

BACKGROUND OF THE INVENTION

Development of new antimicrobials has progressively slowed down since the 1980s, leaving a bleak scenario in the face of emerging multi-drug resistant pathogens. So called 'superbugs' are increasingly recognised as a global threat to public health, driving exploration of new antimicrobials—including inorganic agents, such as those based on copper and silver. These metals have had historical usage and, significantly, are hypothesised to act via a multiplicity of biocidal mechanisms—which could potentially enhance clinical longevity by requiring microorganisms to undergo multiple mutations to gain resistance. Of the two metals, silver has shown greater antimicrobial efficacy: however, cost, in vivo toxicity to the host and chemical instability are likely to limit its utility for clinical applications such as the healing of infected wounds. Copper, whilst generally seen as less efficacious, is inexpensive and, being an essential micronutrient, is better tolerated by humans and other animals, allowing greater doses to be used. However, owing to its lower biocidal efficacy, the development of delivery systems which maximise bioavailability of copper to microbes is critical to its use in clinical settings.

WO 2016/170152 (Medical Research Council) discloses copper oxo-hydroxide nanoparticles compositions in which one or more ligands are non-stoichiometrically substituted for the oxo or hydroxy groups of the copper oxo-hydroxide. Compositions comprising the nanoparticles are disclosed for use as antibacterial compositions capable of releasing free copper.

WO 98/16218 and U.S. Pat. No. 6,197,763 (Pflori limited) describe the use of therapeutic complexes formed between dietary metals, such as copper, manganese or iron, and ligands including ascorbate, aspartate, citrate, histidine, malate, maltol (3-hydroxy-2-methyl-4-pyrone), gluconate, glutamate, glutamine, succinate and tartrate for use in treating gastrointestinal bacterial infections. WO 00/16736 relates to copper cyclic alpha-hydroxyketone complexes as active ingredients in oral care with anti-plaque activity. JP 2002/255956 describes copper-pyrone complexes as anti-fungal agents in foodstuffs. Hudekova et al. (Foli Microbial., 41(6): 473-476, 1996) describes metal ion Kojic acid complexes prepared with Cu, Zn, Mn, Mg or Ni that were tested for anti-bacterial and anti-fungal activities. The copper complexes were found to only be active against *B. subtilis* and *P. aeruginosa*.

The development of approaches for the effective delivery of antimicrobial metal ions, such as copper, remains an unresolved problem in the art, especially for use in a clinical setting.

SUMMARY OF THE INVENTION

Broadly, the present invention is based on the findings that antibacterial compositions comprising a copper hydroxypyrone complex are capable of delivering copper in a bactericidally available form. While strong complexing agents maintain copper in solution, including physiological fluids, and thus are expected to be good delivery vehicles for biocidal copper, the present inventors found that in complexes such as copper EDTA, ligands with excessive affinity for copper have the effect of making a proportion of the copper metal unavailable for interaction with bacteria, thereby significantly suppressing its antibacterial action. On the other hand, copper salts, such as copper chloride, are capable of providing free copper to bacteria and are therefore advantageous over strong copper complexes.

However, these compositions suffer from the disadvantage that their bactericidal effect is diminished in the presence of components of biological relevance, such as proteins. This limitation is clinically relevant since protein is an abundant component in physiological fluids, such as wound exudate.

Accordingly, the present invention provides copper based antibacterial agents that ameliorate both of these disadvantages through the use of amphiphilic copper complexes, for example those formed between copper and hydroxypyrones, such as maltol. This was demonstrated by experiments in which copper was incubated in bacterial media comprising BSA which showed that copper maltol completely suppressed *E. coli* growth at 40 ppm copper, whereas copper chloride only achieved 60% inhibition at 50 ppm copper.

In further aspects, the present invention relates to PEG based-ointments showing that they are particularly effective for topical delivery of amphiphilic complexes of copper. In particular, PEG ointments were shown to limit bacterial growth, even when in the absence of copper agent. However, this bacteriostatic effect is shown herein to become a true biocidal effect when copper hydroxypyrones are added to the PEG.

Surprisingly, it was further noted that PEG ointments containing copper maltol became more efficacious as they aged such that more than 3 weeks after preparation they appeared more efficacious than after a few days of preparation in the porcine model such that log colony forming units of MRSA per gram of skin biopsy were 1.6 log CFU/g versus 5.1 log CFU/g, respectively. Whilst not wishing to be bound by any particular theory the present inventors believe that the association between the two components becomes more advantageous for topical antimicrobial activity over time.

Surprisingly, the antibacterial compositions of the present invention had equivalent antibacterial efficacy to that of PEG ointments containing the antibiotic, mupirocin. While copper is known to be an antimicrobial agent, it is generally an inferior one compared to standard antibiotics. It is therefore surprising that the copper hydroxypyrone complexes of the present invention provide the same outcome as with mupirocin in these experiments. The present inventors believe that this is a consequence of the combination of copper hydroxypyrone complexes and polyalkylene glycol.

A further advantage of the association between copper maltol and PEG, herein referred to as copper maltol-PEG assemblies is that it protects copper complexes from degradation. For example, cupric copper ($Cu^{2+}$) complexed with maltol gradually converts to the cuprous form ($Cu^+$) when in an alkaline solution, as evidenced by the formation of a red precipitate. This effect is presumed to be mediated by maltol which is likely to promote copper reduction. Surprisingly, the addition of polyalkylene glycols such as PEG suppresses this phenomenon. Without wishing to be bound by any particular theory, the formation of copper maltol-PEG assemblies appears to protect copper maltol from degradation, in particular redox degradation that causes $Cu^{2+}$ to be reduced to $Cu^-$, as indicated by a colour change in the copper complexes in the compositions from green ($Cu^{2+}$) to red ($Cu^+$).

Amphiphilic ligands are used to accentuate the bactericidal power of copper. Without wishing to be bound by any particular theory, the inventors expect the amphiphilic ligands' ability to cross membrane barriers to be bactericidally advantageous in that it is likely to promote internalisation of copper into bacterial cells.

PEG ointments comprising amphiphilic complexes, such as maltol, may additionally comprise soluble silicate or colloidal or larger particulate silicates. Evidence suggests that silicate promotes wound healing. Usefully, the present compositions are amenable to the inclusion of silicate such as small amorphous silicate colloids and, importantly, these silicates don't interact with copper as might be normally expected so long as the copper is in a complex, such as with maltol.

In one aspect, the present invention provides an antibacterial composition comprising a polyalkylene glycol and a copper hydroxypyrone complex. Preferably, copper hydroxypyrone complex comprises maltol and/or ethylmaltol. Most preferably, the antibacterial composition comprises copper maltol.

Polyalkylene glycols are a family of polyether compounds that include polyethylene glycol (PEG) and polypropylene glycol. In some embodiments, it is possible to employ combinations of more than one different polyalkylene glycols, e.g. two, three, four or five or more sugars or polyalkylene glycols. In the antibacterial compositions of the present invention, preferably the polyalkylene glycol is polyethylene glycol (PEG) or polypropylene glycol. The compositions formed between the polyalkylene glycol and the copper hydroxypyrone complex will generally be is an ointment or cream and therefore suitable for external application (e.g. topical application) to a subject in need of treatment. Preferably, the ratio of copper to maltol is between 1:0.5 and 1:10, or 1:1 and 1:5, or 1:1 and 1:4.

Preferably, the compositions comprise at least 10% (w/w) of the polyalkylene glycol, more preferably at least 20% (w/w) of the polyalkylene glycol, at least 30% (w/w) of the polyalkylene glycol, at least 40% (w/w) of the polyalkylene glycol, at least 50% (w/w) of the polyalkylene glycol, and optionally at least 60% (w/w) of the polyalkylene glycol.

In some embodiments, the antibacterial composition further comprises a bioavailable form of silicate, whether soluble, particulate or colloidal silicates.

In a further aspect, the present invention provides an antibacterial composition as described herein for use in a method of treating a microbial infection, for example for the treatment of a bacterial infection such as an MRSA infection. In other uses, the compositions of the present invention may be employed prophylactically, for example in the treatment of wounds.

In a further aspect, the present invention provides pharmaceutical compositions comprising the antibacterial composition as described herein.

In a further aspect, the present invention provides the use of an antibacterial composition of the present for the preparation of a medicament for the treatment or prevention of microbial infection.

In a further aspect, the present invention provides a method of treating or preventing a microbial infection, the method comprising administering to a patient in need of treatment a therapeutically effective amount of an antibacterial composition of the present invention.

Embodiments of the present invention will now be described by way of example and not limitation with reference to the accompanying figures. However, various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

DETAILED DESCRIPTION

Formulations and Uses

Figure 1:
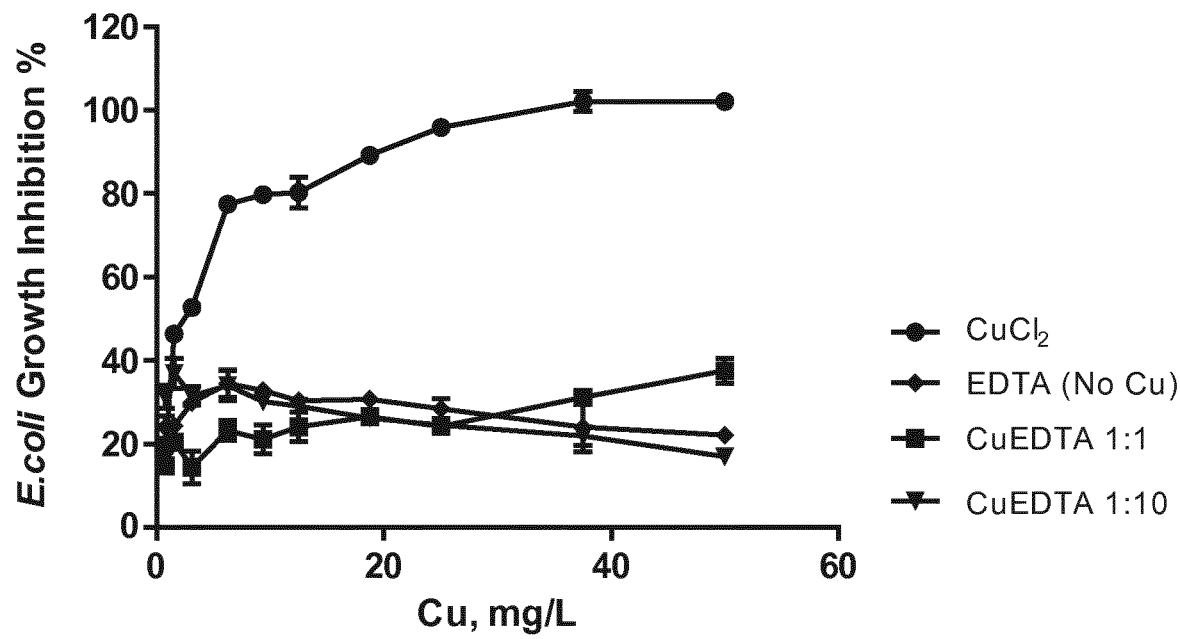
FIG. 1. *E. coli* growth inhibition in HMM (pH 7.2) after 6 hours of incubation with $CuCl_2$, Cu:EDTA complexes with ratio 1:1 and 1:10 and EDTA only with concentrations equivalent to those present in the Cu:EDTA 1:10 complex.

The antibacterial compositions of the present invention may be formulated for use as antibacterial agents or antimicrobial agents, for example for the treatment or prevention of bacterial or microbial infections. Accordingly, the compositions of the present invention may comprise, in addition to one or more of the solid phase materials of the invention, a pharmaceutically acceptable excipient, carrier, buffer, stabiliser or other materials well known to those skilled in the art. Such materials should be non-toxic and should not significantly interfere with the efficacy of the solid phase materials for the application in question.

The term "antibacterial" as used herein includes the treatment or prevention of infections caused by gram negative and gram positive microorganisms including *Escherichia* sp., such as *E. coli, Staphylococcus* sp., such as *S. epidermis, S. aureus* and meticillin-resistant *Staphylococcus aureus* ("MRSA"), *Bacillus* sp., such as *B. subtilis, Pseudomonas* sp., such as *P. aeruginosa, Vibrio* sp., such as *V. fisheri, Streptococcus* sp., such as *S. pyrogenes* and *S. pneumoniae, Klebsiella* sp., *Micrococcus* sp., such as *M. luteus, Clostridium* sp. such as *C. difficile, Acinetobacter* sp. such as *A. baumannii, Mycobacterium* sp., such as *M. tuberculosis* and *Salmonella* sp, or fungi including *Candida* sp., such as *C. albicans*. The term "antimicrobial" as used herein is understood to apply to substances including those which inhibit microbial attachment to surfaces, kill microbes and/or inhibit microbial reproduction. The term "microbe" is understood to include all microorganisms, including bacteria as set out above, as well as fungi such as yeast, archaea and protists. The terms "microbial" and "antimicrobial" should be interpreted accordingly.

The use of the antibacterial compositions of the present invention will very depending on whether the compositions are intended for the treatment or prevention of infection in a human or animal subject, or to provide a surface of an article that is resistant to bacterial or microbial colonisation. Example of the latter application include providing coatings for medical equipment or dressings.

However, as well as having applications for the treatment or prevention of conditions in human subjects, the present invention has application in the veterinary field, for example for use in the treatment of a non-human animal, and more especially non-human mammals such as dogs, cats and horses.

In embodiments in which the compositions are intended for the administration to subject, for example in the treatment of wounds or skin infections, the precise nature of the carrier or other component may be related to the manner or route of administration of the composition, typically via a topical route. This may include formulation of the antibacterial compositions in a solid, semi-solid or gel matrix or in a liquid carrier such as water, petroleum, animal or vegetable oils, mineral oil or synthetic oil. Examples of carriers include physiological saline solution, dextrose or other saccharide solution or glycols such as ethylene glycol, propylene glycol or polyethylene glycol may be included.

The materials and compositions used in accordance with the present invention that are to be given to an individual are preferably administered in a "prophylactically effective amount" or a "therapeutically effective amount" (as the case may be, although prophylaxis may be considered therapy), this being sufficient to show benefit to the individual clinical state. The actual amount administered, and rate and timecourse of administration, will depend on the nature and severity of what is being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

Examples of the techniques and protocols mentioned above can be found in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

In other embodiments, the antibacterial compositions of the present invention may be formulated for topical administration, e.g. in the form of a solid or semi-solid ointment useful in the treatment of wounds, ulcers or the treatment or prevention of bacterial infection. In such applications, polyalkylene glycols are well suited for external, and especially topical, delivery of the materials as they form a cream or an ointment and is available in a range of different molecular weights, allowing the tailoring of viscosity and other physical parameters that may be desirable in the final ointment. In some embodiments, the cream or ointment will preferably comprise a low molecular weight PEG and a high molecular weight PEG and optionally polypropylene glycol. By way of example, the low molecular weight PEG may be a polyethylene glycol having a molar weight between 200 g/mol and 600 g/mol, and more preferably is a polyethylene glycol having a molecular weight between 380 g/mol and 420 g/mol, e.g. a PEG 400. Preferably, the high molecular weight PEG is a polyethylene glycol having a molecular weight between 1500 g/mol and 4000 g/mol, and more preferably is a polyethylene glycol having a molecular weight between 3200 g/mol and 3500 g/mol, e.g. a PEG 3350. In some cases the polyalkylene glycol used in the formulations of the present invention comprises a combination of one or more polyethylene glycols and one of more polypropylene glycols, such as a combination of PEG 400, PEG 3350 and polypropylene glycol. The application of the present invention to topical products has therapeutic use for wound healing and as in anti-infective compositions. In some embodiments of the present invention, topical administration does not include oral administration.

In all aspects of the present invention in which the compositions are formulated for administration to a subject, it is preferred that the pH of the composition or a formulation containing it is raised to a physiological pH, preferably to a pH between 5.0 and 9.0, and more preferably to a pH of between 6.0 and 8.5. The examples show that the compositions of the present invention are capable of making free copper bioavailable under these conditions. Conveniently, this may be done by adding a base, such as sodium hydroxide or sodium carbonate, or an acid such as hydrochloric acid. The aim of this is so that administration to a subject will not result in unintended clinical outcomes, such as pain or inflammation.

In addition to the copper hydroxypyrone complex, the antibacterial compositions of the present invention may comprise a silicate composition, whether in the form of soluble, particulate or colloidal silicates. A particularly preferred form of silicate composition are ultra fine amorphous nanosilicates ("uSANs") in which silica particles having a mean diameter between 0.5 nm and 20 nm are optionally stabilised by one or more stabilising agents. Compositions comprising stabilised nanosilica compositions that include stabilising agents and processes for their production are described in WO 2015/121666 (Medical Research Council) and PCT/EP2017/070183 claiming priority from GB-A-1701827.6, all of which are incorporated by reference in their entirety. Examples of stabilising agents suitable for use with the nanosilica composition of the present invention include polyols, sugars and/or quarternary ammonium salts, such as choline and carnitine. In particular, WO 2015/121666 provides processes for producing a stabilised polymeric silicate composition comprising polymeric silicic acid and nanosilica particles, in which polymerisation of silicates and particle size growth is controlled and the resulting particles are rendered size stable through the combination of silicate concentration, pH and/or stabiliser. In some embodiments, the compositions may additionally be doped with metal cations as these may induce particle size growth and may provide the compositions with useful additional properties.

The nanosilica compositions of the present invention comprise soluble polysilicic acid and nanosilica particles having mean diameters of 20 nm or less, and in some cases mean diameters that are more preferably less than 10 nm, more preferably less than 5 nm, 4 nm, 3 nm, 2 nm, 1 nm or 0.5 nm. In some embodiments, the particles may range from about 0.5 nm to about 2 nm, or from about 0.5 nm to about 3 nm, or from about 0.5 nm to about 4 nm, or from about 0.5 nm to about 5 nm, or from about 0.5 nm to about 10 nm, or from about 0.5 nm to about 15 nm, or from about 0.5 nm to about 20 nm, or from about 5 nm to about 20 nm, or from about 5 nm to about 15 nm, or from about 5 nm to about 10 nm, or from about 10 nm to about 15 nm, or from about 10 nm to about 20 nm, or from about 15 nm to about 20 nm. Preferred compositions include silica particles having a mean diameter between 0.5 and 10 nm and silica particles having a mean diameter between 2 and 5 nm.

The non-soluble nature of the polymeric silicic acid and/or nanosilica particles may be confirmed indirectly by the molybdic acid assay mentioned above as this determines the soluble silicic acid fraction. In general, the materials will be in equilibrium with the soluble silicic acid, with typical soluble silicic acid concentration being about <2 mM at pH<9.0. The nanosilica compositions may be contrasted with more condensed forms of silicates, including larger nanoparticles (e.g. preferably having an average size greater than 50 nm, and more preferably greater than 20 nm), polysilicic acid gels and silicon dioxide ($SiO_2$) the fully condensed form of silicic acid, in which —OH groups are virtually absent. The size of the particles of polysilicic acids can be determined using dynamic light scattering and it is preferred that the measurements are made on freshly prepared samples, if not stabilised. As will be understood by those skilled in the art, the polysilicic acids will be in equilibrium with other silicate species. For example, and depending on the precise conditions present, this may include smaller amounts of soluble silicic acid.

An effective amount of antibacterial compositions herein may be formulated for topical application, e.g. to the skin, nails or hair. These compositions can be in the form of creams, lotions, gels, suspensions, dispersions, microemulsions, nanodispersions, microspheres, hydro gels, emulsions (oil-in-water and water-in-oil, as well as multiple emulsions) and multilaminar gels and the like (see, for example, The Chemistry and Manufacture of Cosmetics, Schlossman et al., 1998), and may be formulated as aqueous or silicone compositions or may be formulated as emulsions of one or more oil phases in an aqueous continuous phase (or an aqueous phase in an oil phase). The type of carrier utilized in the present invention depends on the properties of the topical composition. The carrier can be solid, semi-solid or liquid. Suitable carriers are liquid or semi-solid, such as creams, lotions, gels, sticks, ointments, pastes, sprays and mousses. Specifically, the carrier is in the form of a cream, an ointment, a lotion or a gel, more specifically one which has a sufficient thickness or yield point to prevent the particles from sedimenting. The carrier can itself be inert or it can possess benefits of its own. The carrier should also be physically and chemically compatible with the antibacterial composition or other ingredients formulated in the carrier. Examples of carriers include water, hydroxyethyl cellulose, propylene glycol, butylene glycol and polyethylene glycol, or a combination thereof.

In addition to the therapeutic use of the antibacterial compositions of the present invention, they may also be applied as antimicrobial or antibacterial coatings to articles, for example coatings on substrates which comprise woven fabric, non-woven fabric, plastic, glass and/or metal. The antimicrobial nature of the coatings makes them particularly suitable to be applied to substrates for use in medical or personal care applications. In particular, the coatings are particularly useful on substrates which are in contact with the body, for example with skin or mucous membrane, in normal use, for example dressings, bandages and plasters.

For example, microbial growth is a particular problem when skin or mucous membrane is covered, for example by a wound dressing, nappy or underwear. As soon as skin or mucous membrane becomes covered, the environmental conditions for microbial growth improve. Microbes present on the covered skin or mucous membrane can multiply at enhanced rates, particularly when the environment is moist and/or not exposed to air. Secretions from these microbes include acid or alkali excretions which can alter the pH of the skin, toxin secretion and enzyme secretion, including protease secretion. These secretions and excretions can cause skin and mucous membrane irritation, and in the more severe cases skin or mucous membrane breakdown, such as dermatitis.

Particular conditions which can occur following to the covering of skin or mucous membrane include thrush. Thrush is a fungal infection, by the *Candida* genus of yeast, particularly *Candida albicans*. Symptoms include itching, burning and soreness, and inflammation of the infected area. The wearing of sanitary towels, incontinence pads, nappies and/or tight underwear can produce conditions favourable to *Candida* growth, which can lead to thrush. The coatings of the present invention may be effective against fungi such as yeast, and accordingly it will be understood that providing the coatings of the invention on the above mentioned items may enable the treatment and/or prophylaxis of thrush.

Similarly, contact dermatitis (commonly known as nappy rash) may be caused by the wearing of incontinence pads or nappies. Damp or wet skin loses its structure, high pH can promote bacterial growth and the bacteria can secrete enzymes which break down the skin tissue. This environment can also promote or exacerbate pressure ulcers (commonly known as bed sores), which are particularly problematic when they become infected. The coatings of the present invention have been found to be effective against bacteria, and accordingly it will be understood that providing the coatings of the invention on tampons, sanitary towels, incontinence pads or nappies may enable the treatment and/or prophylaxis of contact dermatitis and/or pressure ulcers.

For similar reasons, contact dermatitis and yeast infections can occur under medical dressings, for example dressings for wounds and burns. An additional consideration with medical dressings is the need to prevent bacterial infection of the wound or burn. When skin is burnt, a large amount of tissue may be damaged which can reduce or destroy the natural barrier properties of skin, and wounds which break the skin also affect the barrier properties of skin. This can lead to opportunistic infection that can delay healing, and to septic shock. Additionally, microbial infection, particularly bacterial infection, can be a problem after surgery. The use of medical or surgical devices, for example implantable medical devices, which are coated with the present antimicrobial coatings may help to prevent or treat post-surgical infection. Accordingly, it will be understood that providing the coatings of the invention on dressings for wounds and/or burns may enable the treatment and/or prophylaxis of contact dermatitis and/or microbial infection.

The antibacterial compositions of the present invention, then, can be used in the manufacture of a medicament for the treatment and/or prophylaxis of microbial infection, and/or of skin or mucous membrane disorders such as inflammation and dermatitis. In particular, the antibacterial or antimicrobial coatings may be useful for the treatment and/or prophylaxis of infection of a wound, infection of a burn, infection of a pressure ulcer, post-surgical infection, thrush, contact dermatitis and pressure ulcers. The microbial infection may be by any microbe, in particular bacteria and/or yeast such as *Staphylococcus* sp., such as *S. aureus*, *Pseudomonas* sp., such as *P. aeruginosa*, *Micrococcus* sp., such as *M. luteus*, *Saccharomyces* sp., such as *S. cerevisiae*, *Candida* sp., such as *C. albicans*, *Staphylococcus* sp., such as *S. epidermis*, *Streptococcus* sp., such as *S. pyrogenes*, *Klebsiella* sp. and *Escherichia* sp., such as *E. coli*, *Chlamydia* sp. The compositions may further be active against viruses or parasites. The medicament may be a substrate coated by the coating methods of the present invention. For example, then, the medicament may be a coated substrate such as a coated medical device, for example an implantable medical device. Examples include a surgical seed, catheter (such as a urinary catheter, a vascular access catheter, an epidural catheter), a vascular access port, an intravascular sensor, a tracheotomy tube, a percutaneous endoscopic gastrostomy tube, an endotracheal tube, an implantable prosthetic device, such as a stent and related short-indwelling or biocontacting devices. The medicament may be a coated substrate such as a coated nappy, sanitary towel, tampon, incontinence pad, dressing such as a wound or burn dressing, bandages or underwear. Many of these substrates (particularly nappies, sanitary towels, incontinence pads and dressings such as wound or burn dressings) comprise a non-woven fabric component, which may be in contact with skin or mucous membrane in normal use. The present inventors have demonstrated that the coatings and coating methods of the present invention are particularly suited to non-woven fabric substrates.

As used herein, the term "non-woven fabric" includes fabrics or textiles formed from a web of fibres. In non-woven fabric, the fibres are not woven or knitted. Non-wovens are typically manufactured by putting small fibers together in the form of a sheet or web, and then binding them mechanically. Example non-woven fabrics include polypropylene non-wovens.

It will be understood that the manufacturing process of the medicament may include providing an antimicrobial coating on a substrate. Accordingly, the manufacture of the medicament may comprise any of the steps of the methods described herein for providing antimicrobial coatings.

The present invention also provides substrates coated by the present methods. The coated substrates may be for use in a method of medical treatment, and include the coated substrates mentioned above as possible medicaments. It will be understood that the present invention also provides a method of medical treatment for the treatment and/or prophylaxis of microbial infection and/or of disorders of the skin or mucous membrane, and the use of the present coated substrates in such methods. The coating methods of the present invention are applicable to coating the substrates mentioned herein, as medicaments or otherwise.

As well as the applications described above, the antimicrobial coatings may also be provided on other equipment for use in medical applications, for example in hospitals. There is significant interest in controlling infection in hospitals, in particular bacterial infection such as MRSA and *Clostridium* difficile. As discussed above, microbial colonisation of surfaces is a particular problem. However, the present coatings have been found to be effective against many species of microbe, and so it will be understood that providing the present antimicrobial coatings on the surface of hospital equipment may be beneficial. Accordingly, substrates which may be coated according to the present invention include medical equipment and devices which contact the body or body fluids in normal use. For example, suitable substrates include tubes, fluid bags, catheters, syringes and surgical equipment such as scalpels and forceps etc. Additionally, other equipment, for example equipment used in hospitals (e.g. healthcare equipment) may be coated according to the present invention, for example gowns (e.g. surgical gowns), surgical masks, protective gloves (e.g. surgical and examination gloves), curtains, uniforms and bedding such as pillow cases, waterproof mattress covers (for example in babies cots and intensive care beds) and sheets.

Alternative healthcare equipment includes surgical draperies, surgical socks, furniture such as tables including bedside tables, beds, and seating surfaces, and other equipment including storage containers, filters, and service trays.

Additionally, the coatings of the invention are useful in coating equipment which it is desirable to keep free of microbes, for example equipment which is used in processing of food, for example kitchen equipment and surfaces, and factory equipment used in the manufacture or processing of food. For example, substrates which can be coated according to the present invention include containers (such as food storage containers), conveyors, blades, mixers, rollers and kitchen utensils (such as cutting and serving implements). Additional substrates include food preparation surfaces, flexible and rigid packaging and door handles.

Additionally, protective clothing worn by workers, for example overalls, gloves, masks and hats could be coated. Other clothing which may be coated includes undergarments, socks, athletic apparel, surgical apparel, healthcare apparel, shoes and boots.

Other substrates suitable for coating include filters, for example medical filters (including respirator filtration media and fluid filtration media), and other filters including HVAC filtration media, water filtration media and fluid filtration media.

Further suitable substrates include currency, debit/credit cards, industrial waste and water handling equipment, petrochemical and crude oil production, distribution and storage equipment and infrastructure. Additional suitable substrates include personal protective equipment and military apparatus such as face masks, respirators, decontamination suits and gloves.

EXPERIMENTAL

Exemplification of Redox Protection

Stocks

A 40 mM copper stock was prepared by dissolving 0.347 g copper chloride dihydrate in 50 mL water. The resulting solution was blue.

A 160 mM maltol stock was prepared by dissolving 1.01 g maltol in 50 mL water and pH adjusting with NaOH (pH>10.5). This produced a clear solution.

Experiment A: Copper Maltol Degradation

The copper and maltol stocks were mixed in water at 1:1 ratios (v:v) producing a green solution. pH was then adjusted to 11.8 with sodium hydroxide to accelerate redox conversion. Overnight, a red precipitate (cuprous hydroxide) deposited at the bottom of the vial.

Experiment B: Copper Maltol-PEG Assemblies Prevent Redox Conversion

Same as experiment A but 30% (w/w) PEG was added. No conversion to cuprous hydroxide was observed even after several days.

Materials and Methods

Preparation of PEG Ointments

General Preparation of PEG Ointments

The PEG ointments are generally composed of 1) a PEG-based phase comprising polyethylene glycol (PEG) and propylene glycol (PPG) and 2) an aqueous phase comprising copper and silicate materials. To prepare 30 g of a PEG-based ointment, 11.4 g of polyethylene glycol 3350 (PEG 3350), 9.75 g of PEG 400 and 3.81 g of propylene glycol (PPG) were weighed into separate falcon tubes and heated up to 65° C. until PEG3350 was fully melted. The PEG400 and PPG were firstly mixed in a 100 ml beaker and melted PEG 3350 was then add and mixed using an overhead stirrer. Copper materials were prepared as per Table 1 and then 5 ml of an aqueous phase is then added to the PEG mixture (as per table below). Finally, pH was adjusted to 7-8 using solutions of 6M HCl or 5M NaOH (measured with pH strips). The final ointments are mixed for at least 5 minutes and transferred into appropriate containers to solidify overnight.

TABLE 1

Preparation of stocks for PEG ointments

| Stock | Protocol |
|---|---|
| (1) CuMaltol, ratio 1:1 Cu0.4M, Maltol 0.4M | A 2M maltol solution was prepared by dissolving 3.5 g of NaOH in 25 ml of UHP water, followed by the addition of 12.6 g of maltol whilst the solution was still warm from the dissolution of NaOH. Once the maltol was fully dissolved the volume was adjusted to 50 ml with UHP water. CuMaltol complex (ratio 1:1) was prepared by diluting this 2M maltol solution in 12 ml of alkaline water (11 ml water + 1 ml 5M NaOH) and then mixing - under vigorous stirring - with 4 ml of 2M CuCl$_2$. |
| (2) 2M CuCl$_2$ | 17.05 g of CuCl$_2$•2H$_2$O were dissolved in UHP water to a final volume of 50 ml. |
| (3) CuEDTA, ratio 1:4 0.2M Cu, 0.8M EDTA | An alkaline solution of EDTA (1M) was prepared by dissolving 4.4 g of NaOH and 11.7 g of EDTA in a total volume of 40 ml. The CuEDTA complex was prepared by mixing 16 ml of alkaline EDTA solution with 2 ml of 5M NaOH and 2 ml of 2M CuCl$_2$. |
| (4) CuMaltol, ratio 1:4 0.4M Cu, 1.6M Maltol | A 2M maltol solution was prepared as described in (1). 4 ml of 2M CuCl$_2$ were added to 16 ml of Maltol solution under vigorous stirring. A thick slurry was formed and manual mixing was required to fully homogenise the complex. |
| (5) 500 mM uSANS | 4 ml of sodium silicate (6.25M Si) was diluted in 44 ml of water. Then the pH was quickly dropped with 2 ml of HCl 37% to pH < 1. |

TABLE 2

Aqueous phase composition of PEG ointments containing ca. 1000 ppm Cu

| Material | Components of aqueous phase |
|---|---|
| PEG only (No copper) | 5 g of UHP water |
| PEG + CuMaltol (ratio 1:1) | 3.8 g of UHP water<br>1.2 ml of CuMaltol (Stock 1) |
| PEG + CuCl$_2$ | 4.8 g of UHP water<br>0.21 ml of 2M CuCl$_2$•2H$_2$O (Stock 2) |
| PEG + CuEDTA (ratio 1:4) | 2.9 g of UHP water<br>2.12 ml of 0.2M CuEDTA (Stock 3) |
| PEG + CuMaltol (ratio 1:4) | 3.8 g UHP water<br>1.2 g CuMaltol (Stock 4) |
| PEG + CuMaltol (ratio 1:4) + Silicate (4-5 mM) | 3.56 g of UHP water<br>0.25 ml of 500 mM uSANS (Stock 5)<br>1.2 g of CuMaltol (Stock 4) |
| PEG + CuMaltol (ratio 1:4) + Silicate (30 mM) | 2.0 g of UHP water<br>1.8 ml of 500 mM uSANS (Stock 5)<br>1.2 g of CuMaltol (Stock 4) |

Preparation of Copper Complexes with EDTA, Maltol and Ethyl Maltol for Antimicrobial Testing Cu-EDTA complexes were freshly prepared by dissolving CuCl$_2$.2H$_2$O and disodium ethylenediaminetetraacetate (EDTA) di-hydrate in UHP water. The pH was adjusted to 7.5±0.2 with 1M NaOH. Various Cu:EDTA ratios were achieved by maintaining concentration copper at 20 mM (ca. 1270 ppm), whilst changing that of EDTA—20 and 200 mM—thus achieving Cu-EDTA ratios of 1:1 and 1:10, respectively.

CuMaltol (ratio 1:1) was prepared by mixing equivalent volumes of 100 mM CuCl$_2$.2H$_2$O solution with an alkaline (pH>11) 100 mM maltol solution and quickly diluting the mixture to 10 mM Cu (final pH of 5.7).

Cu Ethylmaltol (ratio 1:1) was prepared by mixing appropriate volumes of 80 mM CuCl$_2$.2H$_2$O solution with an alkaline (pH>10.5) 20 mM ethylmaltol solution and quickly diluting the mixture to 10 mM Cu and 10 mM ethylmaltol (final pH of 7.2).

CuMaltol (ratio 1:4) was prepared by mixing appropriate volumes of 80 mM CuCl2.2H2O solution with an alkaline (pH>10.5) 60 mM maltol solution and quickly diluting the mixture to 10 mM Cu and 40 mM maltol (final pH of 8.5).

Cu Ethylmaltol (ratio 1:4) was prepared by mixing appropriate volumes of 80 mM CuCl2.2H2O solution with an alkaline (pH>10.5) 60 mM ethylmaltol solution and quickly diluting the mixture to 10 mM Cu and 40 mM ethylmaltol (final pH of 8.5).

Bacterial Work
Heavy Metal MOPS (HMM) Medium, pH 7.2±0.2.

HMM is a defined medium developed for testing heavy metals and here was supplemented with glucose and casamino acids (acid hydrolysate of casein) and optionally with 4% BSA. HMM was prepared from concentrated stock solutions of each reagent, and pH adjusted to 7.2±0.2 (Table 1). Freshly prepared medium was immediately filtered through a 0.22 micron membrane and stored at 4±2° C.

TABLE 3

Composition of HMM medium.

| Reagent | Concentration in HMM medium |
|---|---|
| 3-(N-morpholino)propanesulfonic acid (MOPS) | 40 mM |
| KCl | 50 mM |
| NH$_4$Cl | 10 mM |
| MgSO$_4$ | 0.5 mM |
| FeCl$_3$·6H$_2$O | 1 µM |
| Glycerol-2-Phosphate | 1 mM |
| Glucose | 0.4% (w/v) |
| Casein acid hydrolysate | 0.1% (w/v) |

In Vitro Antibacterial Assay for Liquid Copper Solutions

Antimicrobial activity was assessed through determination of *E. coli* NCTC1110 growth inhibition in the presence of copper compounds. A turbidimetric assay was used to follow bacterial concentration over time as this is proportional to optical density (OD at 595 nm) in liquid medium. Bacterial cultures were grown overnight in HMM at 30° C. under constant shaking (80 rpm). On the day of the assay, the OD of the bacterial suspension was measured at 595 nm on a plate reader and diluted in HMM to achieve an OD of 0.05. Copper stock solutions (refer to "Preparation of copper complexes" section) were sequentially diluted in HMM (with or without 4% BSA) to achieve typical concentrations between 0.8 and 100 mg/L Cu in a volume of 0.1 ml. Next, 0.1 ml of bacterial culture was added and incubated with copper at 30° C. under constant agitation (80 rpm). Final copper concentrations in the assay ranged between 0.4 and 50 ppm, and OD was measured every hour for a typical period of 6 to 8 hours. OD background, i.e. OD absorbance not caused by bacteria, was determined to remove readout interference from copper and broth. Growth inhibition was calculated as follows:

$$\text{Growth Inhibition \%} = \left(\frac{OD\ \text{Control} - OD\ \text{Copper}}{OD\ \text{Control}}\right) \times 100$$

OD control: OD of bacteria incubated in HMM in the absence of copper, after subtraction of OD of medium (no bacteria).

OD copper: OD of bacteria incubated in HMM in the presence of copper, after subtraction of OD of medium plus a matching concentration of copper (no bacteria).

In Vitro *E. Coli* Growth and Bactericidal Effect in the Presence of PEG Ointments PEG ointments were prepared on the day before of the assay (unless otherwise stated) and 0.05 ml or 0.1 ml (10% and 20% of the volume of bacterial culture added, respectively) were transferred with a syringe into wells on 24 well-plate. 0.5 ml of *E. coli* NCTC11100 culture in protein-free HMM—prepared as described in the antimicrobial assay for copper solutions—were added on top of the ointment and incubated for 24 hours at 30° C. with agitation (80 rpm). At 0, 6 and 24 h 0.1 ml were collected and the OD595 nm was measured to follow bacteria growth. Bactericidal effect of PEG ointments was assessed by collecting 5 µl of the bacterial cultures exposed to the PEG after 6 hours of incubation and transferred onto agar plates. After overnight incubation at 30° C., the agar plates were investigated for the presence of *E. coli* colonies.

Determination of Copper Concentration by ICP-OES

Inductively coupled plasma-optical emission spectroscopy (ICP-OES) was used to determine elemental copper concentration. All samples were diluted in 5% HNO3 (v/v) at least 24 hours prior to analysis to fully dissolve copper materials. Calibration standards were matrix-matched in 5% HNO$_3$, ranging from 0.1 to 100 ppm. The line used for copper detection was 324.754 nm.

Gel Release Assay 250 mg of each ointment was transferred into an Eppendorf tube and centrifuged for 2 min at 5000 rpm. Next, 0.75 ml of a solution of 50 mM NaHCO$_3$ (pH 7.0) was carefully transferred into the Eppendorf tube containing the ointment. The tube was left standing (no agitation) at room temperature and an aliquot of ca. 500 ml was collected from the top and analysed by ICP-OES (copper concentration).

In Vivo Testing of PEG Ointments Against a Clinical Pathogen

A porcine model was used to investigate the efficacy of PEG ointments against Methicillin resistant *Staphylococcus aureus* (MRSA). Deep partial thickness wounds (10 mm×7 mm×1.0 mm) were clipped in the paravertebral and thoracic area of the pigs with a specialized electrokeratome fitted with a 7 mm blade and wounds were separated from one another by 2-3 cm. Immediately after wounding, 25 µl of 10$^5$ CFU/ml MRSA USA300 suspension was inoculated into each wound and within 20 minutes, all wounds were treated with ca. 200 mg of ointment. Polyurethane dressings were used to cover each wound after application of ointments. From day 0 to day 4 treatments were applied twice daily and after this (day 5 to day 8) the dose was reduced to one treatment per day only. At day 4 and 8 a skin biopsy was collected and the number of MRSA colonies formed was determined to obtain a total concentration of bacteria per mass of biopsy (CFU/g).

Results

Figure 2:
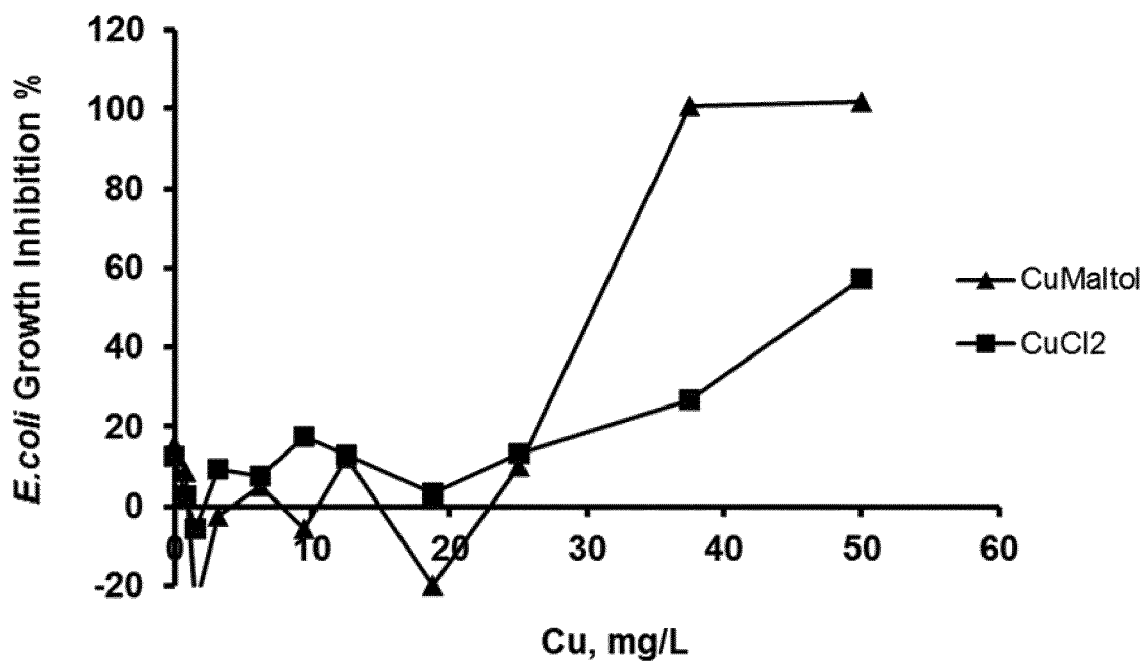
FIG. 2. *E. coli* growth inhibition upon incubation with $CuCl_2$ and CuMaltol (ratio 1:1) in HMM with 4% BSA for 6 hours.

Copper compositions intended for clinical antimicrobial use are required to deliver copper in a bactericidally available form. Strong complexing agents maintain copper in solution, including physiological fluids, and thus are expected to be good delivery vehicles for biocidal copper. However, as illustrated with copper EDTA, ligands with excessive affinity for copper make this metal unavailable for interaction with bacteria thus significantly suppressing its antibacterial action (FIG. 1). Copper salts, such as copper chloride, can provide free copper to bacteria and thus are advantageous over strong copper complexes. However, their bactericidal effect is greatly diminished in the presence of components of biological relevance, such as protein. This limitation is of clinical relevance since protein is an abundant component in physiological fluids, such as wound exudate. The obvious solution to prevent copper from interacting with protein would be to use strong copper complexes but, as shown, these are not efficacious against bacteria. The results provided herein show that the use of amphiphilic complexes, such as maltol, greatly overcomes these issues. This was demonstrated by incubating copper in bacterial media comprising BSA: copper maltol completely suppressed *E. coli* growth at 40 ppm copper whereas copper chloride only achieved 60% inhibition at 50 ppm copper (FIG. 2).

Figure 3:
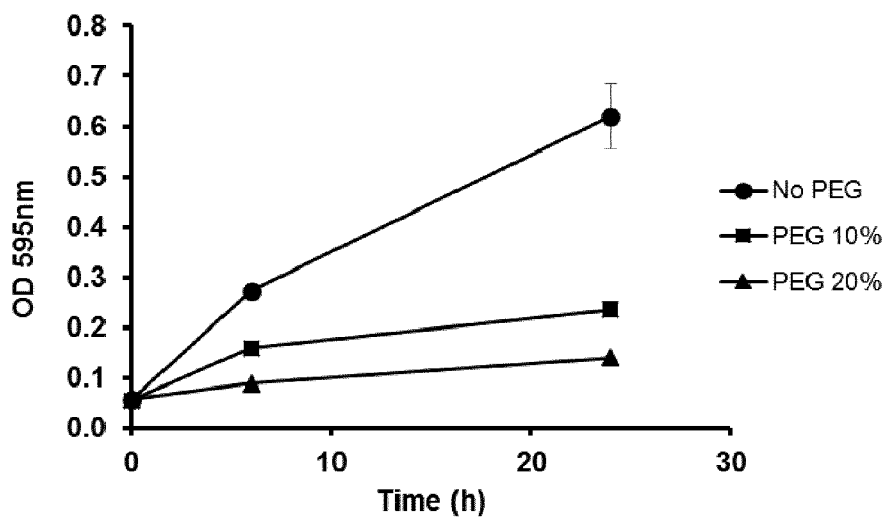
FIG. 3. *E. coli* growth over time—measured as absorbance at OD 595 nm—in the presence of copper-free PEG ointments added as 10 and 20% of the volume of bacterial culture, i.e. 0.05 ml or 0.1 ml of PEG in 0.5 ml of bacterial culture.
Figure 4:
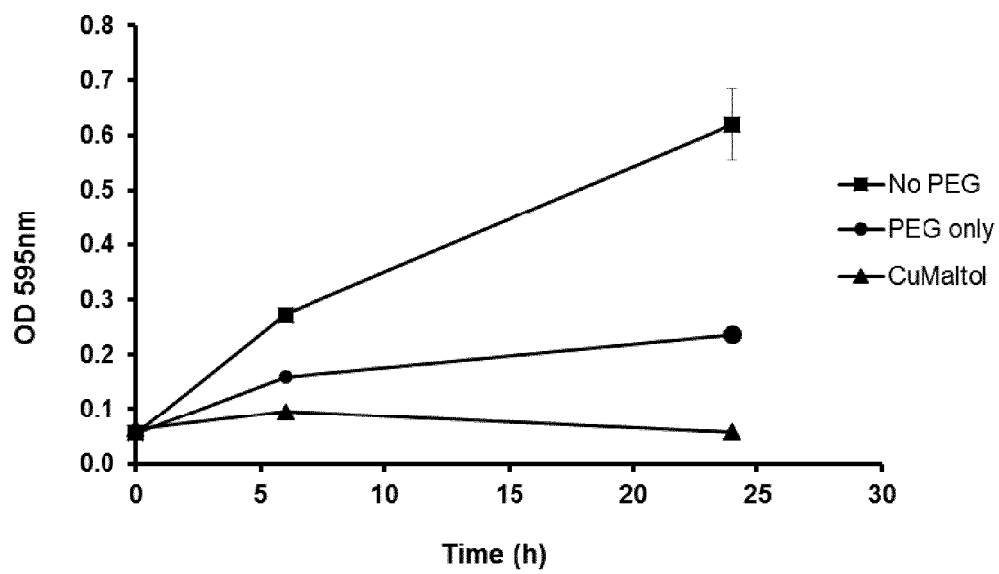
FIG. 4. *E. coli* growth over time—measured as absorbance at OD 595 nm—in HMM after incubation with 10% ointments (see methods).

In further experiments, PEG based-ointments appropriate for topical delivery of copper from amphiphilic complexes of copper were shown to limit bacterial growth, even when in the absence of copper agents (FIG. 3). However, this is solely a bacteriostatic effect—i.e. not bactericidal—and indeed *E. coli* previously exposed to PEG-only ointments were shown to remain viable, as demonstrated in an agar growth assay (Table 1). As such, the inventors discovered that copper agents were required to achieve a true biocidal effect. Firstly, PEG ointments comprising copper maltol have a total suppressive effect upon *E. coli* growth unlike that of PEG-only ointments, which is only partial (FIG. 4). Secondly, bacteria exposed to PEG ointments comprising an amphiphilic complex of copper cease to be viable, as demonstrated in an agar growth assay (Table 4).

Surprisingly, it was further noted that PEG ointments containing copper maltol became more efficacious as they aged such that more than 3 weeks after preparation they appeared more efficacious than after a few days of preparation in the porcine model such that log colony forming units of MRSA per gram of skin biopsy were 1.6 log CFU/g versus 5.1 log CFU/g, respectively. Whilst not wishing to be bound by any particular theory the authors believe that the association between the two components becomes more advantageous for topical antimicrobial activity over time.

Advantageously, the present inventors observed that the antimicrobial activity of copper maltol extends to other copper hydroxypyrone complexes. Copper ethylmaltol is particularly advantageous since, like copper maltol, can be used at various copper:hydroxypyrone ratios and its antimicrobial properties are retained in protein-rich environments.

All documents mentioned in this specification are incorporated herein by reference in their entirety.

TABLE 4

Bactericidal effect of PEG ointments containing in its composition: Si (5 mM uSANS); $CuCl_2 \cdot 2H_2O$; CuEDTA ratio 1:4; CuMaltol ratios 1:1 or 1:4, and CuMaltol ratio 1:4 with 5 mM uSANS (all containing 1000 ppm Cu). These results are representative for concentrations of 10 and 20% of ointment in the total *E. coli* culture after 6 hours exposure.

| PEG ointment | PEG only | +$CuCl_2$ | +CuEDTA 1:4 | +CuMaltol 1:1 | +CuMaltol 1:4 | +CuMaltol 1:4 + Si |
|---|---|---|---|---|---|---|
| Bactericidal (Yes/No) | No | Yes | No | Yes | Yes | Yes |

Figure 5:
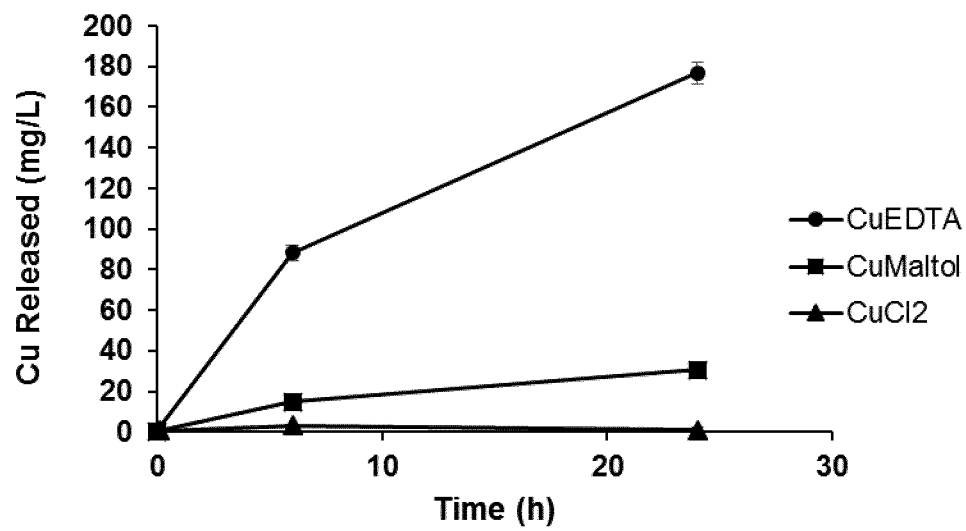
FIG. 5. Copper release in 50 mM $NaHCO_3$ at pH 7.0 from PEG ointments containing CuEDTA, CuMaltol (both with ratios 1:4 Cu:Complexing agent) and $CuCl_2$, (all 1000 ppm Cu).
Figure 6:
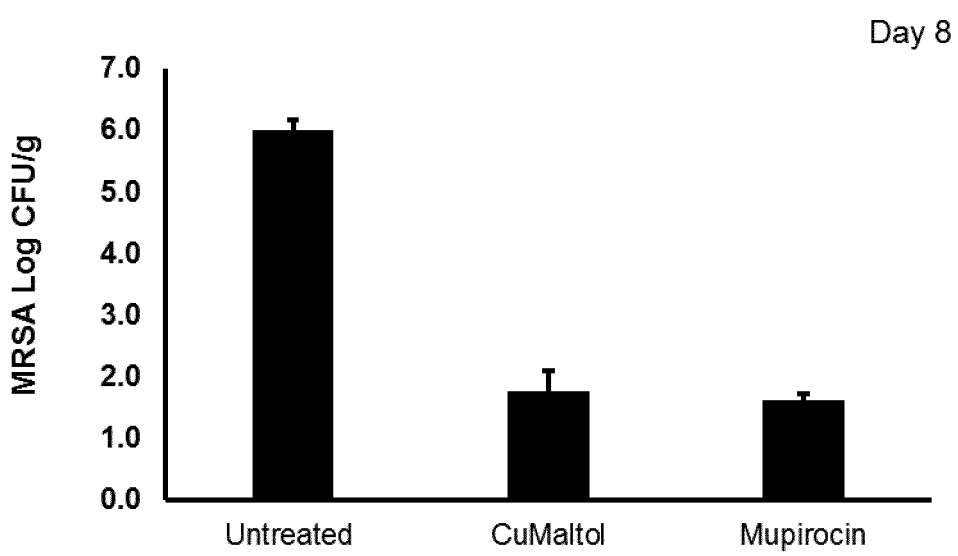
FIG. 6. Bacterial counts in MRSA wound model treated with PEG ointments comprising copper maltol (1:4 Cu:maltol) or Mupirocin (N=3 pigs). Further details are provided in the methods section. PEG ointment. CuMaltol (ratio 1:4) ointment contained 30 mM silicate (uSANS) and 1000 ppm Cu.

Additionally, the present inventors observed that unlike strong complexes, such as copper EDTA, copper hydroxypyrone complexes exhibit a modest release of copper from PEG ointments (FIG. 5). Furthermore, a green, ointment-like, precipitate was generated when copper maltol solutions, which are green, were mixed with PEG solutions. Importantly, the retention of the green colour implies the absence of a direct copper-PEG interaction, as this would generate a blue colour as observed in PEG ointments comprising a copper chloride. Without wishing to be bound by any particular theory, the present inventors believe that copper maltol-PEG assemblies are formed in PEG ointments. This is a particularly advantageous feature in wound healing or treatment of topical infections since it permits controlled release of copper over longer periods. Indeed, this efficacy was demonstrated in the treatment of an vivo wound model (Pig) for MRSA infections. Surprisingly, in some cases, PEG ointments containing copper maltol had equivalent antibacterial efficacy to that of PEG ointments containing the antibiotic, mupirocin (8 day exposure; FIG. 6). While copper is known to be an antimicrobial agent, it is generally an inferior one compared to standard antibiotics. It is therefore surprising that the copper hydroxypyrone complexes of the present invention provide the same outcome as with mupirocin in these experiments. The present inventors believe that this is a consequence of the combination of copper hydroxypyrone complexes and PEG.

Figure 7:
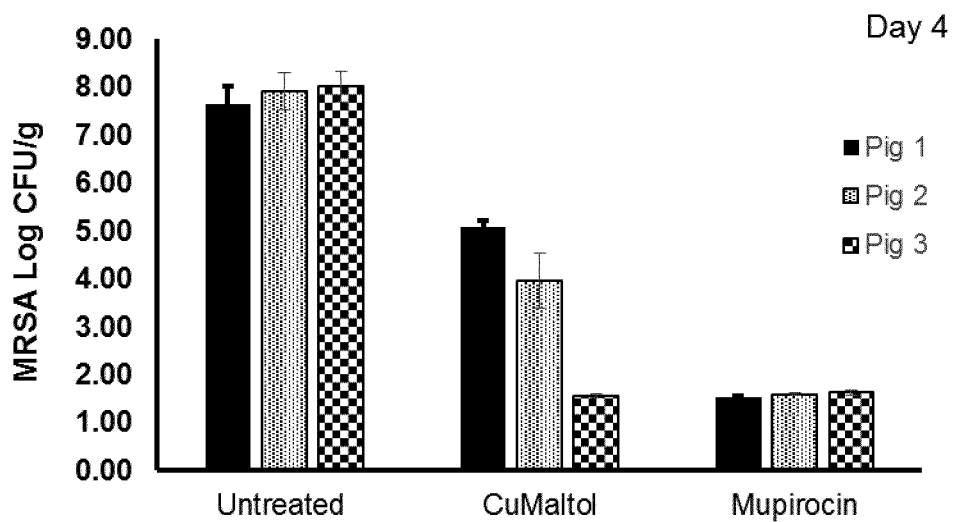
FIG. 7. Bacterial counts in MRSA wound model treated with PEG ointments comprising copper maltol (1:4 Cu:maltol) or Mupirocin. Further details are provided in the methods section.

FIG. 7 shows increase efficacy over time, presumably as the copper maltol pEG assemblies are being formed in the ointment (all pigs were treated from the same batch of ointments but there was a gap of at least 2 weeks in between pig 1 and pig 3 being treated).

Figure 8:
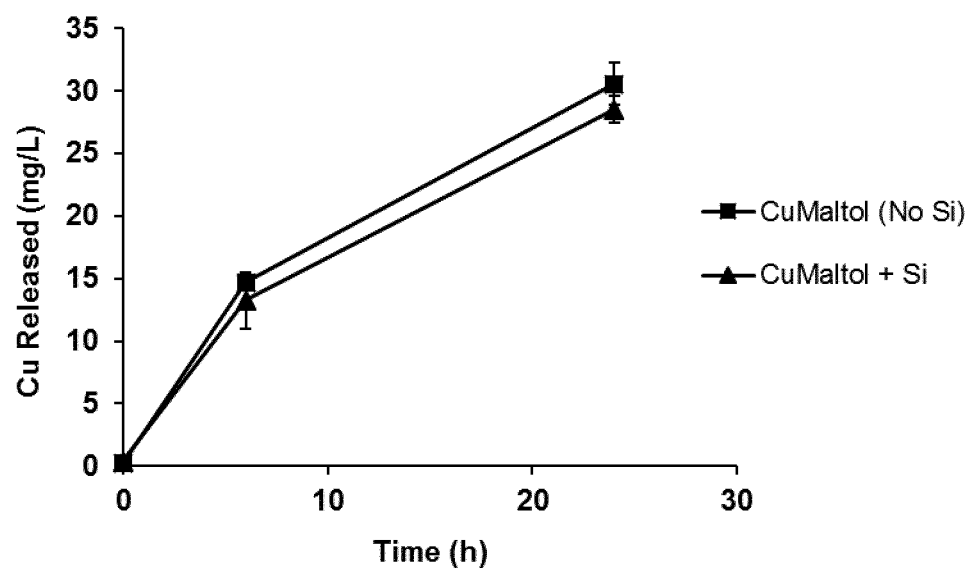
FIG. 8: Copper release from CuMaltol PEG ointments (1000 ppm Cu) with or without silicates in 50 mM $NaHCO_3$ at pH 7.0.
Figure 9:
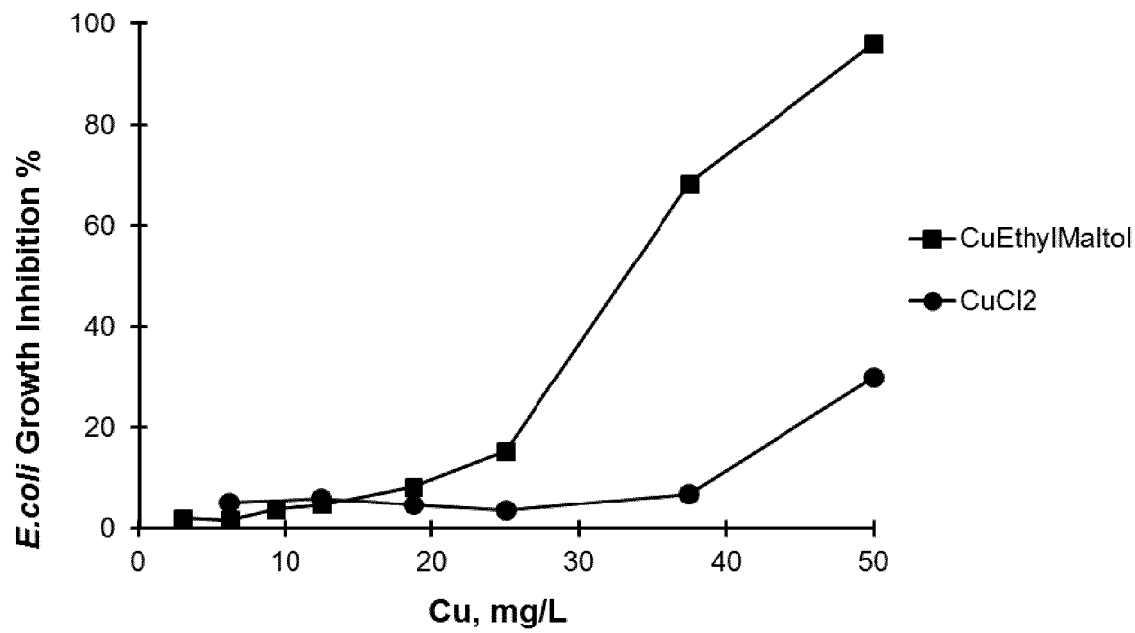
FIG. 9: *E. coli* growth inhibition upon exposure of Cu complexes with ethylmaltol (ratio 1:1) in HMM with 4% BSA for 6 hours.
Figure 10:
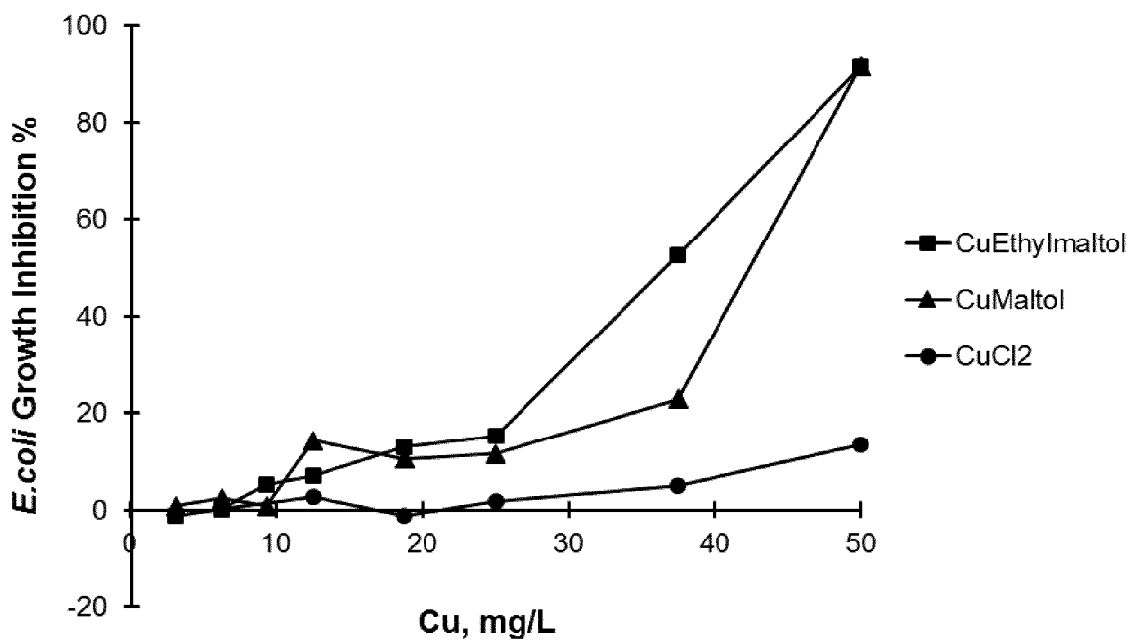
FIG. 10: *E. coli* growth inhibition upon exposure of Cu complexes with maltol and ethylmaltol (ratio 1:4) in HMM with 4% BSA for 6 hours.

FIG. 8 shows that silicate does not interact with copper maltol in PEG ointments as evidence by the equivalent release rates of copper.

The invention claimed is:

1. A method of treating a microbial infection or wound comprising administering an effective amount of an antibacterial composition comprising a polyalkylene glycol and a copper hydroxypyrone complex to a subject in need thereof, wherein the composition comprises at least 20% w/w of the polyalkylene glycol, and wherein the copper hydroxypyrone complex and the polyalkylene glycol form assemblies that protect the copper hydroxypyrone complex from redox degradation.

2. The method of claim 1, wherein the copper hydroxypyrone complex comprises copper maltol and copper ethyl maltol, and the polyakylene glycol is polyethylene glycol (PEG).

3. The method of claim 1, at least 30% (w/w) of the polyalkylene glycol, or at least 50% (w/w) of the polyalkylene glycol.

4. The method of claim 1, wherein:
 (a) the polyalkylene glycol is one or more polyethylene glycols (PEGs) or one or more polypropylene glycols; or
 (b) the polyalkylene glycol comprises a combination of one or more polyethylene glycols and one of more polypropylene glycols.

5. The method of claim 1, wherein the composition is an ointment or cream.

6. The method of claim 2, wherein the ratio of copper to maltol is between 1:0.5 and 1:10, or 1:1 and 1:5, or 1:1 and 1:4.

7. The method of claim 1, wherein the composition further comprises a silicate composition.

8. The method of claim 7, wherein the silicate composition is a nanosilicate.

9. The method of claim 1, wherein the subject is a human subject.

10. The method of claim 1, wherein the composition is for veterinary use.

11. The method of claim 10, wherein the subject is a dog, cat, or horse.

12. The method of claim 1, wherein the microbial infection is a bacterial infection.

13. The method of claim 12, wherein the bacterial infection is caused by a gram-negative or a gram-positive bacterium.

14. The method of claim 12, wherein the bacterial infection is a methicillin-resistant *Staphylococcus Aureus* (MRSA) infection.

15. A method for the treatment or prevention of microbial infection of a wound comprising administering an effective amount of an antibacterial composition comprising a polyalkylene glycol and a copper hydroxypyrone complex to a subject in need thereof, wherein the composition comprises at least 20% w/w of the polyalkylene glycol, and wherein the copper hydroxypyrone complex and the polyalkylene glycol form assemblies that protect the copper hydroxypyrone complex from redox degradation.

16. The method of claim 15, wherein the microbial infection is caused by an *Escherichia* sp., a *Staphylococcus* sp., a *Bacillus* sp., a *Pseudomonas* sp., a *Vibrio* sp., a *Streptococcus* sp., a *Klebsiella* sp., a *Micrococcus* sp., a *Clostridium* sp., an *Acinetobacter* sp., a *Mycobacterium* sp., a *Salmonella* sp., a *Chlamydia* sp., or a fungal species.

17. The method of claim 16, wherein the *Escherichia* sp. is *E. coli*;

wherein the *Staphylococcus* sp. is *S. epidermis, S. aureus* or meticillin-resistant *Staphylococcus Aureus* ("MRSA"); the *Bacillus* sp. is *B. subtilis*; the *Pseudomonas* sp. is *P. aeruginosa*; the *Vibrio* sp. is *V. fisheri*; the *Streptococcus* sp. is *S. pyrogens* or *S. pneumoniae*; the *Micrococcus* sp. is *M. luteus*; the *Clostridium* sp. is *C. difficile*; the *Acinetobacter* sp. is *A. baumannii*; the *Mycobacterium* sp. is *M tuberculosis*; and the fungal species is *Candida* sp. or *C. albicans*.

* * * * *

UNITED STATES PATENT AND TRADEMARK OFFICE
CERTIFICATE OF CORRECTION

PATENT NO. : 11,000,502 B2
APPLICATION NO. : 16/480363
DATED : May 11, 2021
INVENTOR(S) : Jonathan Joseph Powell et al.

Page 1 of 1

It is certified that error appears in the above-identified patent and that said Letters Patent is hereby corrected as shown below:

In the Claims

In Claim 3, Column 16, Line 47, after "The method of claim 1," insert --wherein the composition comprises--

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*